(12) United States Patent
Fujita (10) Patent No.: US 10,882,713 B2
(45) Date of Patent: Jan. 5, 2021

(54) CONTINUOUS BODY FOLDING DEVICE AND FOLDING METHOD

(71) Applicant: ZUIKO CORPORATION, Settu (JP)

(72) Inventor: Hideki Fujita, Settu (JP)

(73) Assignee: ZUIKO CORPORATION, Settu (JP)

( * ) Notice: Subject to any disclaimer, the term of this patent is extended or adjusted under 35 U.S.C. 154(b) by 165 days.

(21) Appl. No.: 15/736,603

(22) PCT Filed: May 24, 2016

(86) PCT No.: PCT/JP2016/065345
§ 371 (c)(1),
(2) Date: Dec. 14, 2017

(87) PCT Pub. No.: WO2016/208311
PCT Pub. Date: Dec. 29, 2016

(65) Prior Publication Data
US 2018/0194588 A1    Jul. 12, 2018

(30) Foreign Application Priority Data
Jun. 24, 2015   (JP) .................................. 2015-126370

(51) Int. Cl.
*B65H 45/08* (2006.01)
*B65H 45/22* (2006.01)
(Continued)

(52) U.S. Cl.
CPC ....... *B65H 45/08* (2013.01); *A61F 13/15747* (2013.01); *A61F 13/15804* (2013.01);
(Continued)

(58) Field of Classification Search
CPC .... B65H 20/10; B65H 2801/57; B65H 45/08; B65H 45/00
(Continued)

(56) References Cited

U.S. PATENT DOCUMENTS 4,614,512 A * 9/1986 Capdeboscq .......... B65H 45/22
                                               198/405
5,997,459 A * 12/1999 Kruger .................. B31F 1/0022
                                               493/161
(Continued)

FOREIGN PATENT DOCUMENTS

JP  2010-227545 A  10/2010
JP  2011-030805 A   2/2011
(Continued)

OTHER PUBLICATIONS

PCT International Search Report of PCT/JP2016/065345, dated Aug. 16, 2016.

*Primary Examiner* — Chelsea E Stinson
(74) *Attorney, Agent, or Firm* — Manabu Kanesaka (57) ABSTRACT

A continuous body folding device includes a conveying part having a moving surface that moves while suctioning and holding a first region of a continuous body, the conveying part conveying the continuous body in the longitudinal direction thereof; a first folding reference part in which a first endless belt, which moves in a first circulatory pathway along a first virtual plane including the moving surface, moves along a first reference segment adjacent to a virtual line of the continuous body in the same direction at the same speed as the moving surface; and first guiding members that are disposed along the first reference segment, contact a second region of the continuous body, and fold the continuous body along the virtual line and move the second region toward the first region so that the angle formed by the first and second regions becomes smaller as the continuous body is conveyed downstream.

6 Claims, 6 Drawing Sheets

(51) Int. Cl.
   *B65H 37/06*   (2006.01)
   *A61F 13/15*   (2006.01)
   *B65H 20/10*   (2006.01)

(52) U.S. Cl.
   CPC ............ *B65H 20/10* (2013.01); *B65H 37/06* (2013.01); *B65H 45/22* (2013.01); *B65H 2301/45* (2013.01); *B65H 2404/1532* (2013.01); *B65H 2404/256* (2013.01); *B65H 2701/19* (2013.01); *B65H 2801/57* (2013.01)

(58) Field of Classification Search
   USPC ........................................ 493/405, 441, 442
   See application file for complete search history.

(56) References Cited

U.S. PATENT DOCUMENTS

| | | | | |
|---|---|---|---|---|
| 6,210,309 | B1* | 4/2001 | Smithe | B65H 45/22 493/248 |
| 8,257,535 | B2* | 9/2012 | Yamamoto | A61F 13/15747 156/204 |
| 9,314,380 | B2* | 4/2016 | Yamamoto | A61F 13/15747 |
| 9,918,881 | B2* | 3/2018 | Schoon | A61F 13/15747 |
| 2005/0096205 | A1* | 5/2005 | Allen | B65H 45/08 493/418 |
| 2007/0129230 | A1* | 6/2007 | Sosalla | A61F 13/15747 493/441 |
| 2010/0179042 | A1* | 7/2010 | Yamamoto | A61F 13/15747 493/379 |
| 2013/0203580 | A1* | 8/2013 | Lenser | A61F 13/15747 493/442 |
| 2013/0296152 | A1* | 11/2013 | Murakami | A61F 13/15747 493/405 |
| 2014/0303587 | A1 | 10/2014 | Back et al. | |
| 2017/0304124 | A1* | 10/2017 | Lenser | A61F 13/15747 |
| 2018/0194588 | A1* | 7/2018 | Fujita | B65H 45/22 |

FOREIGN PATENT DOCUMENTS

| | | |
|---|---|---|
| JP | 2012-095807 A | 5/2012 |
| JP | 2013-013465 A | 1/2013 |
| WO | 2010/101283 A1 | 9/2010 |
| WO | 2012/060249 A1 | 5/2012 |

* cited by examiner

Prior Art

Fig. 6 (b)

Prior Art

Fig. 7
Prior Art

CONTINUOUS BODY FOLDING DEVICE AND FOLDING METHOD

RELATED APPLICATIONS

The present application is National Phase of International Application No. PCT/JP2016/065345 filed May 24, 2016, and claims priority from Japanese Application No. 2015-126370, filed Jun. 24, 2015, the disclosure of which is hereby incorporated by reference herein in its entirety.

FIELD OF THE INVENTION

The present invention relates to a folding device and a folding method, and more particularly, it relates to a folding device and a folding method for a continuous body for folding a belt-like continuous body during conveyance thereof.

BACKGROUND OF THE INVENTION

A continuous body folding device is used, for example, in production of an absorbent article such as a disposable diaper.

Figure 7:
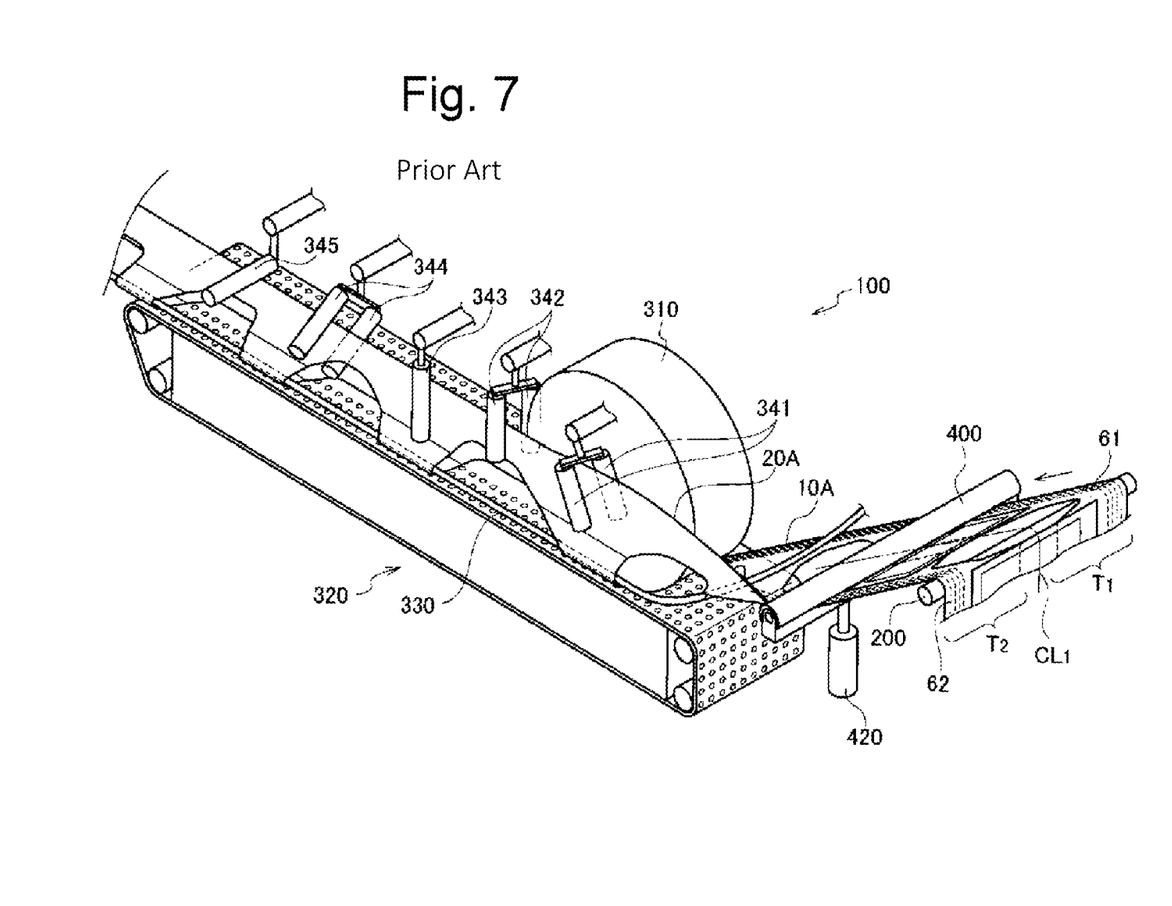
FIG. 7 is a perspective view of a continuous body folding device. (Conventional Example)

FIG. 7 is a perspective view of a continuous body folding device 100 used in production of so-called disposable diaper underpants. As illustrated in FIG. 7, a continuous body includes: first and second portions 61 and 62 spaced from each other and extending in parallel to each other; and absorbers disposed across the first and second portions 61 and 62 and joined to the first and second portions 61 and 62. The continuous body is in a belt shape, and is divided into a first region T1 disposed on the side of the first portion 61 and a second region T2 disposed on the side of the second portion 62 by an imaginary line CL1 extending in a longitudinal direction of the continuous body in the width-directional center of the continuous body. The absorbers are disposed at constant intervals along the imaginary line CL1.

As illustrated in FIG. 7, the continuous body is conveyed to a reference roller 200 in such a manner that the first region T1 and the second region T2 are included in the same plane. A large diameter roller 310, a belt conveyor 320, a folding reference point bar 330, and guide members 341 to 345 are disposed on the downstream side in the conveyance direction from the reference roller 200.

The first region T1 of the continuous body passes between the large diameter roller 310 and the belt conveyor 320, and is then conveyed in the longitudinal direction of the continuous body while being suction-held by the belt conveyor 320.

The folding reference point bar 330 has a linear portion disposed on the downstream side in the conveyance direction from the large diameter roller 310 to be adjacent to the imaginary line CL1 of the continuous body.

The guide members 341 to 345 come into contact with a portion of the second region T2 of the continuous body opposing a portion of the first region T1 of the continuous body suction-held by the belt conveyor 320. The continuous body is folded along the imaginary line CL1 of the continuous body adjacent to the linear portion of the folding reference point bar 330, and the second region T2 of the continuous body is inclined along the guide members 341 to 345 to be folded over the first region T1.

Figures 6A, 6B:
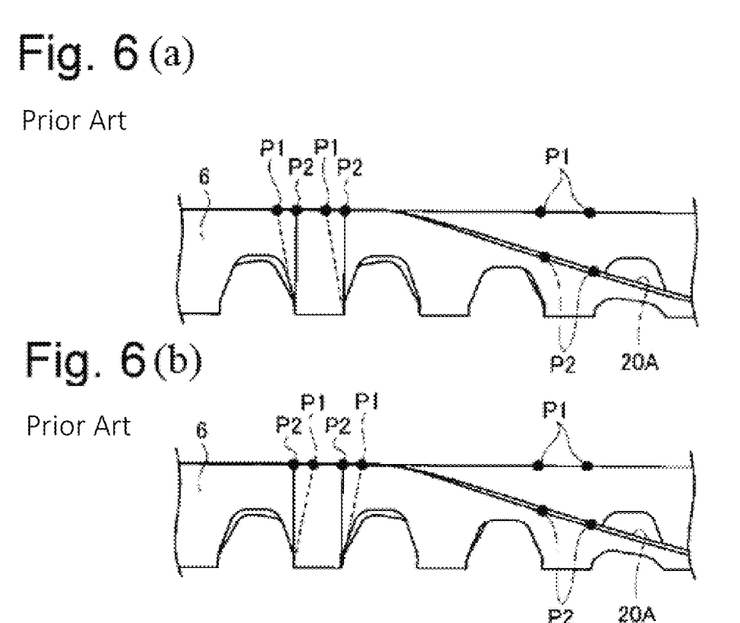
FIGS. 6(a) and 6(b) are explanatory diagrams illustrating a phase shift. (Conventional Example)

As schematically illustrated in FIG. 6, in a portion of a continuous body 6 where a second region is folded over a first region, a phase shift that is a shift in the relative position between a reference point P1 in the first region and a reference point P2 in the second region, which should essentially overlap with each other, may occur in some cases. In order to adjust such a phase shift, a variable roller 400 for pressing the continuous body in a position between the reference roller 200 and the folding reference point bar 330, and a position changing section 420 for changing the position of the variable roller 400 are provided as illustrated in FIG. 7. The position changing section 420 changes the magnitude of pressing the continuous body by the variable roller 400 so as to change at least one of a length of the conveyance locus of one side edge 10A of the continuous body and a length of the conveyance locus of the other side edge 20A (see, for example, Patent Document 1).

CITATION LIST

Patent Document

[Patent Document 1] Japanese Laid-Open Patent Publication No. 2011-30805

SUMMARY OF THE INVENTION

Technical Problem

In such a continuous body folding device, the continuous body under conveyance comes into slide contact with the linear portion of the folding reference point bar 330 in a stationary state. Therefore, a resistance force by friction works on the continuous body so as to disturb the conveyance state of the continuous body, and hence, the phase shift between the first region and the second region easily occurs in the portion where the second region of the continuous body is folded over the first region. As a result, it is necessary to take, for example, measures to reduce the frictional resistance of the folding reference point bar 330, and measures to adjust the conveyance state of the continuous body by using the variable roller 400, and thus, it is not easy to stabilize the operation of folding a continuous body.

In consideration of such practical situations, a problem to be solved by the present invention is to provide a folding device and a folding method for a continuous body capable of easily stabilizing an operation of folding a continuous body.

Solution to Problem

For the purpose of solving the above-described problem, the present invention provides a continuous body folding device configured as follows.

A continuous body folding device is an apparatus for folding a belt-like continuous body along an imaginary line that extends in a longitudinal direction of the continuous body in a width-direction center of the continuous body and divides the continuous body into a first region and a second region. The continuous body folding device includes: (a) a conveying part that has a moving surface moving with the first region of the continuous body suction-held thereon, and conveys the continuous body in such a manner that the longitudinal direction of a suction-held portion of the first region of the continuous body suction-held on the moving surface accords with a moving direction of movement of the moving surface; (b) a first folding reference part that includes a first endless belt moving through a first circulation path along a first imaginary plane including the moving surface, the first circulation path including a first reference segment in which the first endless belt is adjacent to the imaginary line of the continuous body on an opposite side to the moving surface when the first region of the continuous body is suction-held on the moving surface, the first endless belt moving, in the first reference segment, in the same direction as the moving direction of the movement of the moving surface at the same speed as a moving speed of the movement of the moving surface; and (c) a first guide member that is disposed along the first reference segment, comes into contact with an adjacent portion of the second region of the continuous body adjacent to the suction-held portion, and moves, toward the first region, the adjacent portion of the second region of the continuous body in such a manner that an angle between the first region and the second region of the continuous body in a cross-section perpendicular to the imaginary line of the continuous body is reduced toward a downstream side in a conveyance direction of the continuous body.

In the above-described structure, while the continuous body is being conveyed with the first region suction-held on the moving surface of the conveying part, the angle between the first region and the second region is reduced by the first guide member. Since the first endless belt is adjacent to the imaginary line of the continuous body in the first reference segment, the continuous body can be folded along the imaginary line of the continuous body. Since the first endless belt moves through the first circulation path along the first imaginary plane including the moving surface of the conveying part, the angle between the first region and the second region of the continuous body can be made acute. Therefore, after passing through the first folding reference part and the first guide member, the second region can be easily folded over the first region of the continuous body.

When the above-described structure is employed, even if the first endless belt comes into contact with the continuous body in the first reference segment, the first endless belt moves in the same direction at the same speed as the continuous body, and hence a force resistive to the conveyance of the continuous body is not generated. A force resistive to the conveyance of the continuous body can be a factor for disturbing the operation of folding the continuous body, but since such a force is not generated, the operation of folding the continuous body can be easily stabilized.

The continuous body folding device preferably further includes: (d) a second folding reference part that includes a second endless belt moving through a second circulation path along a second imaginary plane perpendicular to the moving surface and parallel to the moving direction of the movement of the moving surface, the second circulation path including a second reference segment in which the second endless belt is adjacent to the imaginary line of the continuous body on an opposite side to the moving surface when the first region of the continuous body is suction-held on the moving surface, the second endless belt moving, in the second reference segment, in the same direction as the moving direction of the movement of the moving surface at the same speed as the moving speed of the movement of the moving surface; and (e) a second guide member that is disposed along the second reference segment, comes into contact with the adjacent portion of the second region of the continuous body adjacent to the suction-held portion, and moves, toward the first region, the adjacent portion of the second region of the continuous body in such a manner that the angle between the first region and the second region of the continuous body in the cross-section perpendicular to the imaginary line of the continuous body is reduced toward the downstream side in the conveyance direction of the continuous body.

In this case, a segment where the continuous body is folded is elongated, so that the operation of folding the continuous body can be further stabilized.

The continuous body folding device more preferably further includes: (f) an opposing position shift detection unit that detects, in a portion of the continuous body having passed through the first guide member, an opposing position shift that is a shift in relative position between a side of a side edge and a side of a folding line of the continuous body; and (g) a control unit that relatively changes the speed of the first endless belt and the speed of the second endless belt with respect to the moving speed of the movement of the moving surface when the opposing position shift detection unit detects the opposing position shift beyond an acceptable level.

In this case, in the occurrence of an opposing position shift that is a shift in relative position between the side of a side edge and the side of a folding line of the continuous body that should essentially oppose each other in a portion of the continuous body where the second region is folded over the first region, the opposing position shift can be eliminated.

Besides, for the purpose of solving the above-described problem, the present invention provides a continuous body folding method configured as follows.

A continuous body folding method is a method for folding a belt-like continuous body along an imaginary line that extends in a longitudinal direction of the continuous body in a width-direction center of the continuous body and divides the continuous body into a first region and a second region. The continuous body folding method includes: (a) a conveying step of suction-holding the first region of the continuous body on a moving surface under movement, and conveying the continuous body in such a manner that the longitudinal direction of a suction-held portion of the first region of the continuous body suction-held on the moving surface accords with a moving direction of movement of the moving surface; (b) a first folding reference step of moving a first endless belt through a first circulation path along a first imaginary plane including the moving surface, the first circulation path including a first reference segment in which the first endless belt is adjacent to the imaginary line of the continuous body on an opposite side to the moving surface when the first region of the continuous body is suction-held on the moving surface, the first endless belt moving, in the first reference segment, in the same direction as the moving direction of the movement of the moving surface at the same speed as a moving speed of the movement of the moving surface; and (c) a first guiding step of causing a first guide member disposed along the first reference segment to come into contact with an adjacent portion of the second region of the continuous body adjacent to the suction-held portion, and moving, toward the first region, the adjacent portion of the second region of the continuous body in such a manner that an angle between the first region and the second region of the continuous body in a cross-section perpendicular to the imaginary line of the continuous body is reduced toward a downstream side in a conveyance direction of the continuous body.

In the above-described method, while the continuous body is being conveyed with the first region suction-held on the moving surface in the conveying step, the angle between the first region and the second region is reduced in the first guiding step. Since the first endless belt is adjacent to the imaginary line of the continuous body in the first reference segment, the continuous body can be folded along the imaginary line of the continuous body. Since the first endless belt moves through the first circulation path along the first imaginary plane including the moving surface of the conveying part, the angle between the first region and the second region of the continuous body can be made acute. Therefore, after completing the first folding reference step and the first guiding step, the second region of the continuous body can be easily folded over the first region.

In the above-described method, even if the first endless belt comes into contact with the continuous body in the first reference segment, the first endless belt moves in the same direction at the same speed as the continuous body, and hence a force resistive to the conveyance of the continuous body is not generated. A force resistive to the conveyance of the continuous body can be a factor for disturbing the operation of folding the continuous body, but since such a force is not generated, the operation of folding the continuous body can be easily stabilized.

The continuous body folding method preferably further includes: (d) a second folding reference step of moving a second endless belt through a second circulation path along a second imaginary plane perpendicular to the moving surface and parallel to the moving direction of the movement of the moving surface, the second circulation path including a second reference segment in which the second endless belt is adjacent to the imaginary line of the continuous body on an opposite side to the moving surface when the first region of the continuous body is suction-held on the moving surface, the second endless belt moving, in the second reference segment, in the same direction as the moving direction of the movement of the moving surface at the same speed as the moving speed of the movement of the moving surface; and (e) a second guiding step of causing a second guide member disposed along the second reference segment to come into contact with the adjacent portion of the second region of the continuous body adjacent to the suction-held portion, and moving, toward the first region, the adjacent portion of the second region of the continuous body in such a manner that the angle between the first region and the second region of the continuous body in the cross-section perpendicular to the imaginary line of the continuous body is reduced toward the downstream side in the conveyance direction of the continuous body.

In this case, a segment where the continuous body is folded is elongated, so that the operation of folding the continuous body can be further stabilized.

The continuous body folding method more preferably further includes: (f) an opposing position shift detecting step of detecting, in a portion of the continuous body having completed the first guiding step, an opposing position shift that is a shift in relative position between a side of a side edge and a side of a folding line of the continuous body; and (g) a controlling step of relatively changing the speed of the first endless belt and the speed of the second endless belt with respect to the moving speed of the movement of the moving surface when the opposing position shift beyond an acceptable level is detected in the opposing position shift detecting step.

In this case, in the occurrence of an opposing position shift that is a shift in relative position between the side of a side edge and the side of a folding line of the continuous body that should essentially oppose each other in a portion of the continuous body where the second region is folded over the first region, the opposing position shift can be eliminated.

Advantageous Effects of the Invention

According to the present invention, an operation of folding a continuous body can be easily stabilized.

DESCRIPTION OF EMBODIMENTS

An example of the present invention will now be described as a preferred embodiment with reference to the accompanying drawings.

Example 1

A continuous body folding device and a continuous body folding method of Example 1 will now be described with reference to FIGS. 1 to 5.

Figure 1:
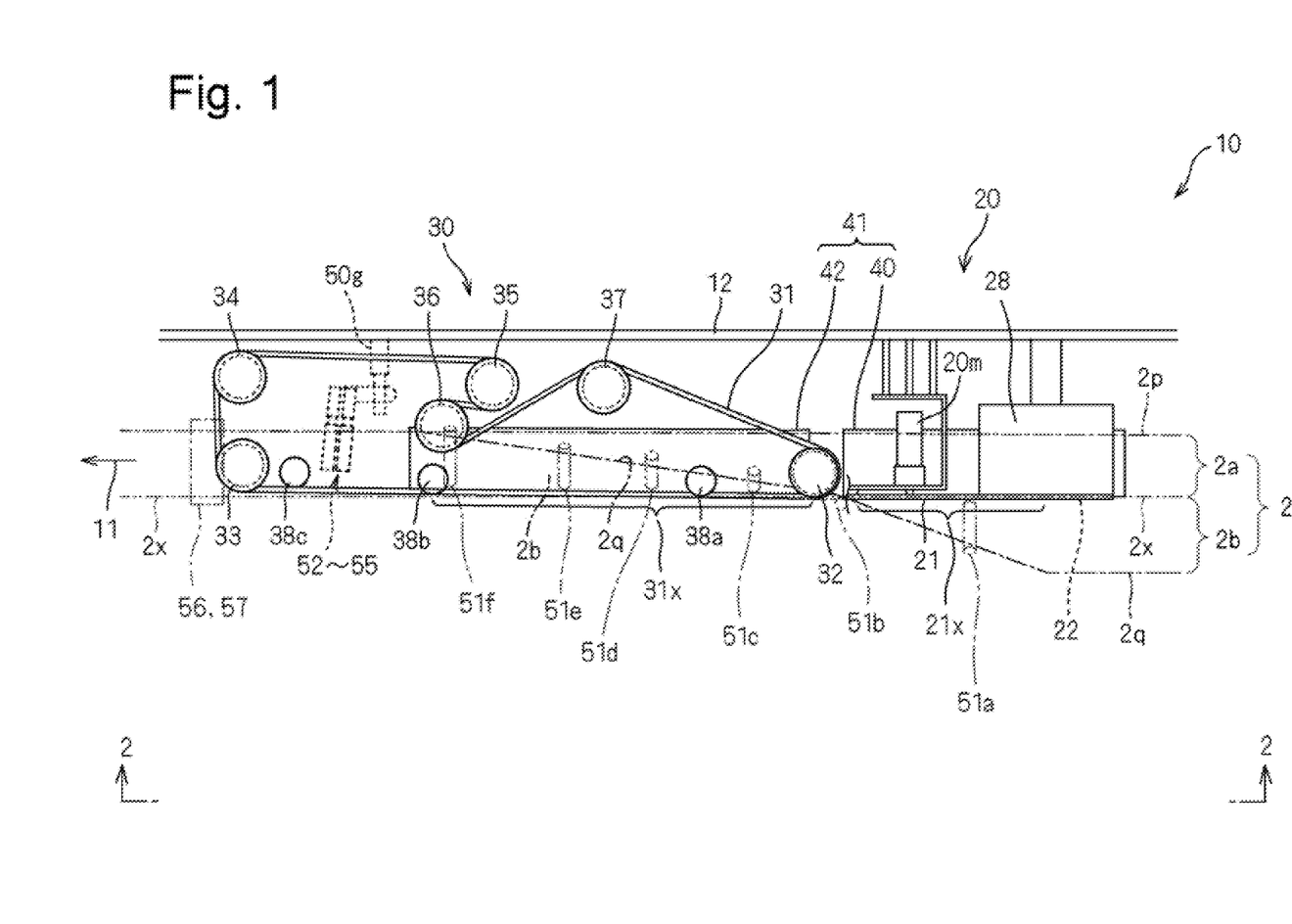
FIG. 1 is a main part plan view of a continuous body folding device. (Example 1)
Figure 2:
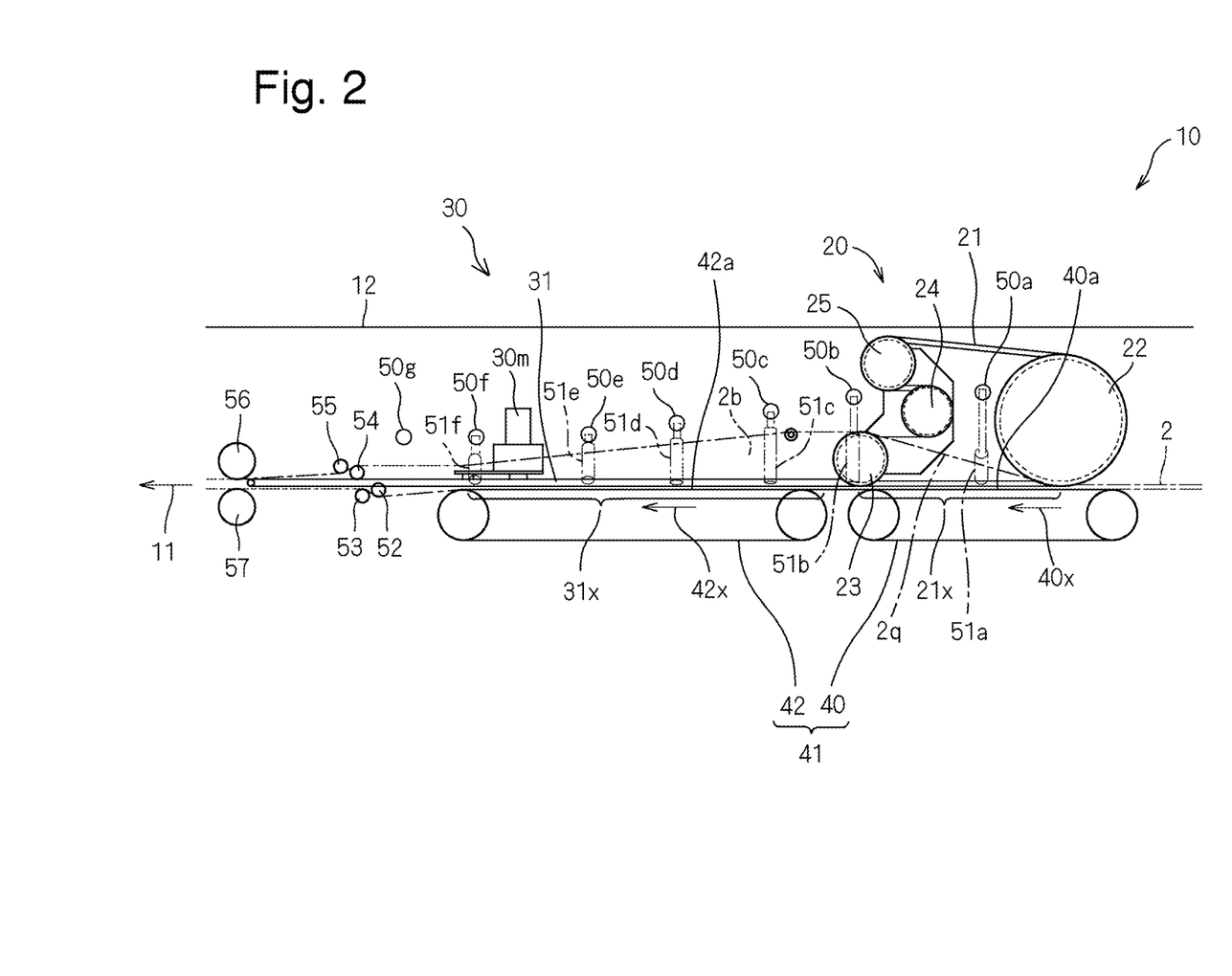
FIG. 2 is a view taken along 2-2 of FIG. 1, namely a main part side view of the continuous body folding device. (Example 1)

FIG. 1 is a main part plan view conceptually illustrating the configuration of a continuous body folding device 10 (hereinafter, sometimes simply referred to as the "folding device 10"). FIG. 2 is a main part side view conceptually illustrating the configuration of the folding device 10. Incidentally, for simplicity of understanding, some elements are illustrated in merely one of FIGS. 1 and 2 and omitted in the other.

As illustrated in FIGS. 1 and 2, the folding device 10 basically includes a conveying part 41, a first folding reference part 30, a second folding reference part 20, first guide members 51c to 51f, and second guide members 51a and 51b. The folding device 10 folds a belt-like continuous body 2 during conveyance thereof.

As illustrated with chain lines in FIG. 1, a continuous body 2 is divided, by an imaginary line 2x extending in the longitudinal direction of the continuous body 2 in the width-direction center of the continuous body 2, into a first region 2a disposed along a first side edge 2p and a second region 2b disposed along a second side edge 2q. The continuous body 2 is conveyed in the longitudinal direction of the continuous body 2 as illustrated with an arrow 11, and is folded in half along the imaginary line 2x during passage through the folding device 10, so as to fold the second region 2b over the first region 2a. Incidentally, a case where the second side edge 2q is overlapped with the first side edge 2p when the continuous body 2 is folded in half is illustrated in the drawings, but the continuous body may be folded in half with the first edge 2p and the second edge 2q spaced from each other.

FIGS. 3(a) and 3(b) are explanatory diagrams schematically illustrating the continuous body 2 used in production of disposal diaper pants. As illustrated in FIG. 3(a), absorbers 4 are disposed at a constant pitch in the longitudinal direction, and a hole 8 for forming an opening for a leg of the disposal diaper pants is formed between the absorbers 4 adjacent to each other. The continuous body 2 is conveyed in the direction illustrated with the arrow 11, and is folded in half as illustrated in FIG. 3(b) by passing through the folding device 10. The continuous body 2 thus folded in half is cut in cut positions 2k illustrated with chain lines in FIG. 3(b) after joining the first region 2a and the second 2b to each other in the vicinity of the cut positions 2k.

The conveying part 41 includes belt conveyors 40 and 42 illustrated in FIG. 2 and conveyance motors 40m and 42m (see FIG. 5) described later. Each of the belt conveyors 40 and 42 suction-holds the first region 2a of the continuous body 2 on a top surface of an upper portion moving on the upper side of a circulating belt member, namely, on a moving surface 40a or 42a.

Specifically, in the belt member of each of the belt conveyors 40 and 42, a through-hole not illustrated is formed. In a space surrounded by the belt member of the belt conveyor 40 or 42, a suction box not illustrated that has an opening opposing the upper portion of the belt member of the belt conveyor 40 or 42, and is connected to a vacuum source is disposed. Thus, air is suctioned through the through-hole formed in the upper portion of the belt member of the belt conveyor 40 or 42, so that the first region 2a of the continuous body 2 can be suction-held on the moving surface 40a or 42a of the belt conveyor 40 or 42.

The moving surface 40a or 42a of the belt conveyor 40 or 42 conveys the continuous body 2 while moving in a direction illustrated with an arrow 40x or 42x while suction-holding the first region 2a of the continuous body 2 in such a manner that the longitudinal direction of a suction-held portion of the first region 2a of the continuous body 2 suction-held on the moving surface 40a or 42a of the belt conveyor 40 or 42 can accord with a moving direction of movement of the moving surface 40a or 42a.

Incidentally, a portion suction-held on the moving surface 40a or 42a of the belt conveyor 40 or 42 may be the whole or a part in the width direction of the first region 2a of the continuous body 2. For example, a portion of the first region 2a of the continuous body 2 illustrated in FIG. 1 excluding areas in the vicinity of the first side edge 2p and the imaginary line 2x may be suction-held on the moving surface 40a or 42a of the belt conveyor 40 or 42.

As illustrated in FIGS. 1 and 2, the first folding reference part 30 is disposed on the downstream side in the conveyance direction of the continuous body 2, and the second folding reference part 20 is disposed on the upstream side in the conveyance direction of the continuous body 2.

As illustrated in FIG. 1, the first folding reference part 30 includes a first endless belt 31, first to sixth pulleys 32 to 37, auxiliary pulleys 38a to 38c, and a first folding drive motor 30m (see FIG. 2).

The fourth pulley 35 is rotatively driven by the first folding drive motor 30m, so that the first endless belt 31 can move through a first circulation path along a first imaginary plane including the moving surface 42a of the belt conveyor 42 disposed on the downstream side in the conveyance direction. The first circulation path is defined by the first to sixth pulleys 32 to 37. The first circulation path includes a linear first reference segment 31x in which the first endless belt 31 moves between the first and second pulleys 32 and 33. When the continuous body 2 is conveyed with the first region 2a thereof suction-held on the moving surface 42a of the belt conveyor 42 disposed on the downstream side in the conveyance direction of the continuous body 2, a portion of the first endless belt 31 moving through the first reference segment 31x is adjacent to the imaginary line 2x of the continuous body 2 on the opposite side to the moving surface 42a, and moves in the same direction as the direction of the movement of the moving surface 42a at the same speed as a moving speed of the movement of the moving surface 42a. The auxiliary pulleys 38a to 38c disposed between the first and second pulleys 32 and 33 prevent the first endless belt 31 from meandering.

Figure 4:
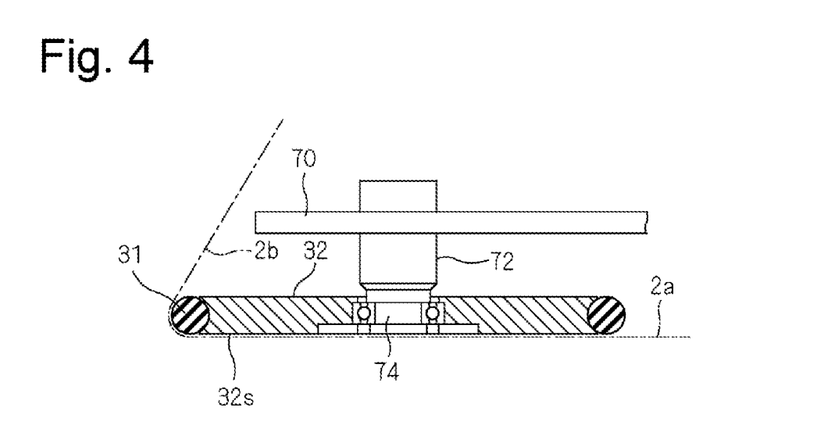
FIG. 4 is a main part sectional view illustrating a supporting structure for a pulley. (Example 1)

FIG. 4 is a main part sectional view illustrating a supporting structure for the first pulley 32. As illustrated in FIG. 4, the first pulley 32 is rotatably supported, via a bearing 74, on a lower end of a support shaft 72 perpendicularly fixed on a support plate 70. The support plate 70 is fixed on a side wall 12 so as to extend along the moving surface 42a of the belt conveyor 42 disposed on the downstream side in the conveyance direction illustrated in FIG. 2 to be parallel or substantially parallel to the moving surface 42a. The other pulleys 33 to 37 and 38a to 38c are similarly rotatably supported.

In order to provide a space between a side surface 32s of the first pulley 32 and the first region 2a of the continuous body 2 suction-held to be conveyed on the moving surface 42a of the belt conveyor 42 disposed on the downstream side in the conveyance direction, for example, the width of the first pulley 32 is set to be smaller than the diameter of the first endless belt 31. The first endless belt 31 preferably has a circular cross-section, but one having a cross-section in another shape such as an ellipse or a rectangle may be used. The first endless belt 31 may be a timing belt. When the first endless belt 31 is a timing belt, occurrence of a shift between the first endless belt 31 and each of the pulleys 32 to 37 and 38a to 38c can be prevented, and a folding operation can be more precisely performed.

As illustrated in FIG. 2, the second folding reference part 20 includes a second endless belt 21, first to fourth pulleys 22 to 25, and a second folding drive motor 20m (see FIG.

The third pulley 24 is rotatively driven by the second folding drive motor 20m, so that the second endless belt 21 can move through a second circulation path along a second imaginary plane, which is perpendicular to a plane including the moving surface 40a of the belt conveyor 40 disposed on the upstream side in the conveyance direction of the continuous body 2, and is parallel to the direction of the movement of the moving surface 40a of the belt conveyor 40. The second circulation path is defined by the first to fourth pulleys 22 to 25. The second circulation path includes a linear second reference segment 21x in which the second endless belt 21 moves between the first and second pulleys 22 and 23. The second reference segment 21x extends beyond the first reference segment 31x toward the downstream side in the conveyance direction of the continuous body 2. When the continuous body 2 is conveyed with the first region 2a thereof suction-held on the moving surface 40a of the belt conveyor 40, a portion of the second endless belt 21 moving through the second reference segment 21x is adjacent to the imaginary line 2x of the continuous body 2 on the opposite side to the moving surface 40a, and moves in the same direction as the direction of the movement of the moving surface 40a at the same speed as a moving speed of the movement of the moving surface 40a.

The second endless belt 21 preferably has a circular cross-section, but one having a cross-section in another shape such as an ellipse or a rectangle may be used. The second endless belt 21 may be a timing belt. When the second endless belt 21 is a timing belt, occurrence of a shift between the second endless belt 21 and each of the pulleys 22 to 25 can be prevented, and the folding operation can be more precisely performed.

As illustrated in FIG. 1, the first pulley 22 is provided at an end of the large diameter roller 28. The large diameter roller 28 is disposed to have an outer circumferential surface opposing the moving surface 40*a* of the belt conveyor 40 disposed on the upstream side in the conveyance direction, and to have a shaft direction perpendicular to the moving direction of the moving surface 40*a* of the belt conveyor 40. The first region 2*a* of the continuous body 2 passes between the large diameter roller 28 and the moving surface 40*a* of the belt conveyor 40.

FIG. 2 illustrates a case where the continuous body 2 enters between the large diameter roller 28 and the moving surface 40*a* of the belt conveyor 40 in parallel to the moving surface 40*a* of the belt conveyor 40. The continuous body 2 may be caused to enter between the large diameter roller 28 and the moving surface 40*a* of the belt conveyor 40 along the large diameter roller 28 in a direction inclined against the moving surface 40*a* of the belt conveyor 40.

As illustrated in FIG. 2, support members 50*a* to 50*g* are provided on the side wall 12 of the folding device 10. Guide members 51*a* to 51*f* are respectively attached to the support members 50*a* to 50*f* as conceptually illustrated with chain lines. The guide members 51*a* to 51*f* have a structure similar to that of guide members 341 to 345 illustrated in FIG. 7, and are attached respectively to the support members 50*a* to 50*f* so that tip sides of the guide members 51*a* to 51*f* can come into contact with the second region 2*b* of the continuous body 2 under conveyance. Each of the guide members 51*a* to 51*f* may have a surface always stationary, or a movable surface. For example, each of the guide members 51*a* to 51*f* may have a cylindrical rotatable outer circumference. The guide members 51*a* to 51*f* are attached respectively to the support members 50*a* to 50*f* so as to come into contact with a first main surface, out of a pair of main surfaces of the second region 2*b* of the continuous body 2, continuous to a main surface of the first region 2*a* of the continuous body 2 suction-held on the moving surfaces 40*a* and 42*a* of the belt conveyors 40 and 42, and so as to reduce an angle between the first region 2*a* and the second region 2*b* of the continuous body 2 toward the downstream side in the conveyance direction of the continuous body 2. Incidentally, guide members to be brought into contact with the other main surface, out of the pair of main surfaces of the second region 2*b* of the continuous body 2, continuous to the other main surface of the first region 2*a* of the continuous body 2 and not suction-held on the moving surfaces 40*a* and 42*a* of the belt conveyors 40 and 42 may be additionally provided.

For example, in a view taken from the downstream side in the conveyance direction of the continuous body 2 toward the upstream side in the conveyance direction of the continuous body 2, the guide members 51*a* to 51*f* in a rod shape are radially disposed around the imaginary line 2*x* of the continuous body 2 so that tips of the guide members 51*a* to 51*f* can substantially point toward the imaginary line 2*x* of the continuous body 2, and that a guide member closer to the downstream side in the conveyance direction can make a smaller angle against the first region 2*a* of the continuous body 2. Each of the guide members 51*a* to 51*f* may be in the shape of a plate or a block apart from a rod.

In FIG. 2, the guide members 51*a* and 51*b* respectively attached to the support members 50*a* and 50*b* on the upstream side in the conveyance direction are second guide members, which make an angle obtuse between the suction-held portion of the first region 2*a* of the continuous body 2 suction-held on the moving surface 40*a* of the belt conveyor 40 and an adjacent portion of the second region 2*b* adjacent to the suction-held portion, and make the obtuse angle smaller toward the downstream side in the conveyance direction.

In FIG. 2, the guide members 51*c* to 51*f* respectively attached to the support members 50*c* to 50*f* on the downstream side in the conveyance direction are first guide members, which make an angle acute between the suction-held portion of the first region 2*a* of the continuous body 2 suction-held on the moving surface 42*a* of the belt conveyor 42 and the adjacent portion of the second region 2*b* adjacent to the suction-held portion, and make the acute angle smaller toward the downstream side in the conveyance direction.

On the support member 50*g* disposed on the most downstream side in the conveyance direction, a first pair of rollers 52 and 53 and a second pair of rollers 54 and 55 are attached as conceptually illustrated in FIG. 1. As illustrated in FIG. 2, the first region 2*a* passes between the first pair of rollers 52 and 53, the second region 2*b* passes between the second pair of rollers 54 and 55, and then the continuous body 2 passes between a third pair of rollers 56 and 57 with the second region 2*b* folded over the first region 2*a*.

Figure 5:
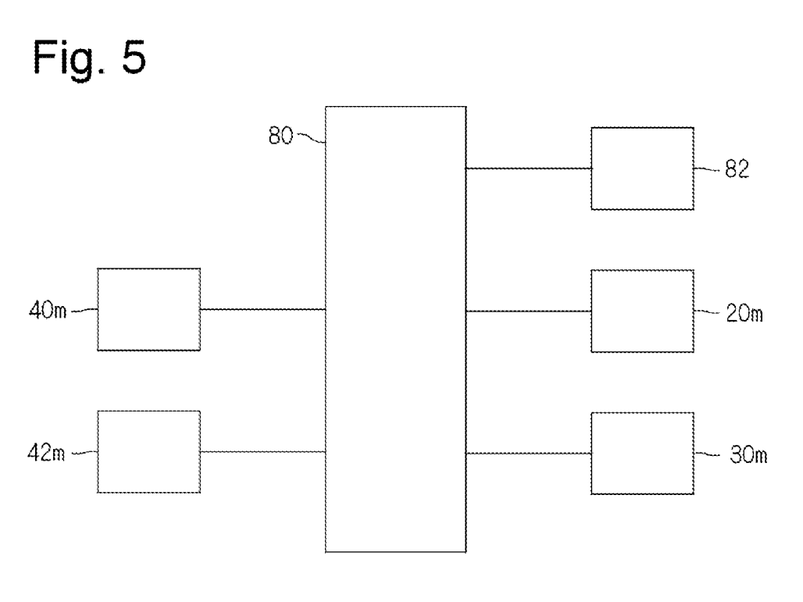
FIG. 5 is a block diagram of a control system. (Example 1).

FIG. 5 is a block diagram illustrating the configuration of a control system of the folding device 10. As illustrated in FIG. 5, a control unit 80 is connected to the conveyance motors 40*m* and 42*m* respectively driving the belt conveyors 40 and 42, the first folding drive motor 30*m* driving the first endless belt 31, the second folding drive motor 20*m* driving the second endless belt 21, and an opposing position shift detection unit 82.

Figure 3:
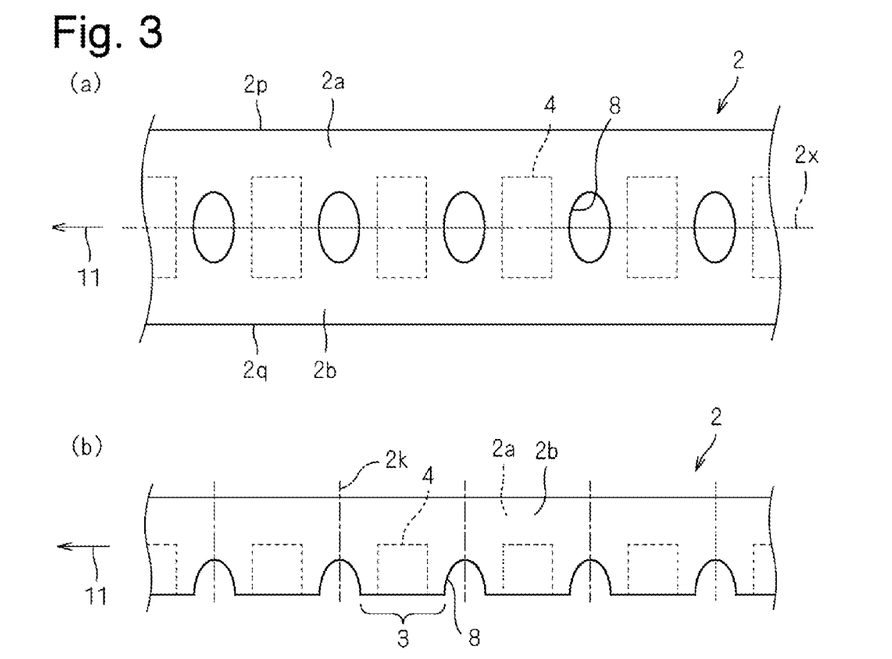
FIGS. 3(a) and 3(b) are explanatory diagrams of a continuous body. (Example 1)

The opposing position shift detection unit 82 detects a shift in relative position between sides of the side edges 2*p* and 2*q* of the continuous body 2 and a side of a folding line (a side of the imaginary line 2*x*) that should essentially oppose each other, namely, an opposing position shift. The opposing position shift detection unit 82 includes, for example, a sensor for detecting marks precedently provided in prescribed positions in the sides of the side edges 2*p* and 2*q* of the continuous body 2 and the side of the folding line (the side of the imaginary line 2*x*), and the opposing position shift is detected based on timing of the sensor detecting the respective marks. In a case where disposable diaper pants are to be produced by using the continuous body 2, the opposing position shift detection unit 82 may include a camera for taking an image of a crotch portion 3 or the hole 8 illustrated in FIG. 3(*b*), and may detect an opposing position shift by extracting, from an image taken by the camera, features such as a direction of the folding line in the crotch portion 3, the shape or the area of the hole 8 and the like. The sensor or the camera of the opposing position shift detection unit 82 is provided in the vicinity of the first and second pairs of rollers 52, 53, 54 and 55, or on the downstream side from the first and second pairs of rollers 52, 53, 54 and 55.

After loading the continuous body 2 on the folding device 10 in a standstill state and before a conveying speed is increased up to a steady-state operation speed, the control unit 80 synchronously changes the rotational speeds of the motors 20*m*, 30*m*, 40*m* and 42*m* so that the moving speeds of the moving surfaces 40*a* and 42*a* of the belt conveyors 40 and 42, the moving speed of the first endless belt 31 in the first reference segment 31*x*, and the moving speed of the second endless belt 21 in the second reference segment 21*x* can be the same.

If the opposing position detection unit 82 detects an opposing position shift beyond an acceptable level during an operation at the steady-state operating speed, the control unit 80 changes, for eliminating the opposing position shift, the rotational speeds of the first and second folding drive motors 30*m* and 20*m* to relatively change the speed of the first endless belt 31 and the speed of the second endless belt 21 with respect to the moving speeds of the moving surfaces 40*a* and 42*a*.

Specifically, if the side of the folding line (the side of the imaginary line 2*x*) is shifted in position from the side of the side edge 2*p* or 2*q* toward the upstream side in the conveyance direction of the continuous body 2, the rotational speeds of the first and second folding drive motors 30*m* and 20*m* are increased by a prescribed increment to increase the conveyance speed of the side of the folding line (the side of the imaginary line 2*x*). If the side of the folding line (the side of the imaginary line 2*x*) is shifted in position from the side of the side edge 2*p* or 2*q* toward the downstream side in the conveyance direction of the continuous body 2, the rotational speeds of the first and second folding drive motors 30*m* and 20*m* are decreased by a prescribed decrement to decrease the conveyance speed of the side of the folding line (the side of the imaginary line 2*x*).

In this manner, in the occurrence of an opposing position shift that is a shift in relative position between the sides of the side edges 2*p* and 2*q* and the side of the folding line (the side of the imaginary line 2*x*) of the continuous body 2 that should essentially oppose each other in the portion of the continuous body 2 where the second region 2*b* is folded over the first region 2*a*, the opposing position shift can be eliminated. A production rate of products using the continuous body 2 is not varied unless the speed of the belt conveyors 40 and 42 are changed.

It is noted that the opposing position shift detection unit 82 may be omitted. Besides, with the control unit 80 omitted, the rotational speeds of the motors 20*m*, 30*m*, 40*m* and 42*m* may be manually controlled.

Next, an operation of folding the continuous body 2 by the folding device 10 will be described.

The first region 2*a* of the continuous body 2 is suction-held on the moving surfaces 40*a* and 42*a* of the belt conveyors 40 and 42. The continuous body 2 is conveyed in the longitudinal direction in accordance with the movement of the moving surfaces 40*a* and 42*a* of the belt conveyors 40 and 42.

The continuous body 2 passes between the large diameter roller 28 and the moving surface 40*a* of the belt conveyor 40 disposed on the upstream side in the conveyance direction to be conveyed with the first region 2*a* suction-held on the moving surface 40*a*. At this point, the second guide members 51*a* and 51*b* attached to the support members 50*a* and 50*b* come into contact with the adjacent portion of the second region 2*b* of the continuous body 2 adjacent to the suction-held portion of the first region 2*a* suction-held on the moving surface 40*a* of the belt conveyor 40, and change the inclination of the adjacent portion of the second region 2*b* of the continuous body 2 in such a manner as to raise the second side edge 2*q* of the continuous body 2. Since the portion of the second endless belt 21 moving through the second reference segment 21*x* is adjacent to the imaginary line 2*x* of the continuous body 2, the continuous body 2 is folded along the imaginary line 2*x*, and the angle between the first region 2*a* and the second region 2*b* in a cross-section perpendicular to the imaginary line 2*x* is reduced toward the downstream side. The angle between the first region 2*a* and the second region 2*b* in the cross-section perpendicular to the imaginary line 2*x* is reduced from 180° to about 90° toward the downstream side in the conveyance direction.

Subsequently, the continuous body 2 is conveyed while suction-held on the moving surface 42*a* of the belt conveyor 42 disposed on the downstream side in the conveyance direction. At this point, the first guide members 51*c* to 51*f* attached to the support members 50*c* to 50*f* come into contact with the adjacent portion of the second region 2*b* of the continuous body 2 adjacent to the suction-held portion of the first region 2*a* suction-held on the moving surface 42*a* of the belt conveyor 42, and change the inclination of the adjacent portion of the second region 2*b* in such a manner that the second region 2*b* of the continuous body 2 comes down to be folded over the first region 2*a*. Since the portion of the first endless belt 31 moving through the first reference segment 31*x* is adjacent to the imaginary line 2*x* of the continuous body 2, the continuous body 2 is further folded along the imaginary line 2*x* of the continuous body 2, and the angle between the first region 2*a* and the second region 2*b* in the cross-section perpendicular to the imaginary line 2*x* is reduced toward the downstream side in the conveyance direction. The angle between the first region 2*a* and the second region 2*b* in the cross-section perpendicular to the imaginary line 2*x* is reduced from about 90° to about 0°.

Next, the continuous body 2 passes between the first to third pairs of the rollers 52 and 53, 54 and 55, and 56 and 57, and as a result, the second region 2*b* is folded over the first region 2*a*.

When the folding device has the structure described so far, while the continuous body 2 is being conveyed with the first region 2*a* suction-held on the moving surfaces 40*a* and 42*a* of the conveying part, the angle between the first region 2*a* and the second region 2*b* is reduced by the first guide members 51*c* to 51*f* and the second guide members 51*a* and 51*b*. Since the first endless belt 31 is adjacent to the imaginary line 2*x* of the continuous body 2 in the first reference segment 31*x* and the second endless belt 21 is adjacent to the imaginary line 2*x* of the continuous body 2 in the second reference segment 21*x*, the continuous body 2 can be folded along the imaginary line 2*x* of the continuous body 2.

Since the first endless belt 31 moves through the first circulation path along the first imaginary plane including the moving surface 42*a* of the conveying part, the angle between the first region 2*a* and the second region 2*b* of the continuous body 2 can be made acute. Therefore, after passing through the first folding reference part 30 and the first guide members 51*c* to 51*f*, the second region 2*b* can be easily folded over the first region 2*a* of the continuous body 2.

Even if the first endless belt 31 comes into contact with the continuous body 2 in the first reference segment 31*x*, the first endless belt 31 moves in the same direction at the same speed as the continuous body 2, and hence a force resistive to the conveyance of the continuous body 2 is not generated. Besides, even if the second endless belt 21 comes into contact with the continuous body 2 in the second reference segment 21*x*, the second endless belt 21 moves in the same direction at the same speed as the continuous body 2, and hence a force resistive to the conveyance of the continuous body 2 is not generated. A force resistive to the conveyance of the continuous body 2 can be a factor for disturbing the operation of folding the continuous body 2, but since such a force is not generated, the operation of folding the continuous body 2 can be easily stabilized.

Since the first folding reference part 30, the first guide members 51*c* to 51*f*, the second folding reference part 20 and the second guide members 51*a* and 51*b* are provided, a segment in which the continuous body 2 is folded is elongated, so that the operation of folding the continuous body 2 can be further stabilized.

When the opposing position shift detection unit 82 and the control unit 80 are provided, in the occurrence of an opposing position shift that is a shift in relative position between the sides of the side edges 2p and 2q and the side of the folding line (the side of the imaginary line 2x) of the continuous body 2 that should essentially oppose each other in the portion of the continuous body 2 where the second region 2b is folded over the first region 2a, the opposing position shift can be eliminated.

Next, a method for folding a continuous body using the folding device 10 will be described.

The method for folding a continuous body using the folding device 10 is a method for folding the continuous body 2 along the imaginary line 2x extending in the longitudinal direction of the continuous body 2 in the width-direction center of the continuous body 2 so as to divide the continuous body 2 into the first region 2a and the second region 2b, and includes (1) a conveying step, (2) a first folding reference step, (3) a first guiding step, (4) a second folding reference step, (5) a second guiding step, (6) an opposing position shift detecting step, and (7) a controlling step.

(1) In the conveying step, the first region 2a of the continuous body 2 is suction-held on the moving surfaces 40a and 42a under movement, so as to convey the continuous body 2 in such a manner that the longitudinal direction of the suction-held portion of the first region 2a of the continuous body 2 suction-held on the moving surfaces 40a and 42a can accord with the moving direction of the movement of the moving surfaces 40a and 42a.

(2) In the first folding reference step, the first endless belt 31 moves through the first circulation path along the first imaginary plane including the moving surface 42a. The first circulation path includes the first reference segment 31x in which the first endless belt 31 is adjacent to the imaginary line 2x of the continuous body 2 on the opposite side to the moving surface 42a when the first region 2a of the continuous body 2 is suction-held on the moving surface 42a. The first endless belt 31 moves, in the first reference segment 31x, in the same direction as the moving direction of the movement of the moving surface 42a at the same speed as the moving speed of the movement of the moving surface 42a.

(3) In the first guiding step, the first guide members 51c to 51f disposed along the first reference segment 31x come into contact with the adjacent portion of the second region 2b of the continuous body 2 adjacent to the suction-held portion, and move the adjacent portion of the second region 2b of the continuous body 2 toward the first region so that the angle between the first region 2a and the second region 2b of the continuous body 2 in the cross-section perpendicular to the imaginary line 2x of the continuous body 2 can be reduced toward the downstream side in the conveyance direction of the continuous body 2.

(4) In the second folding reference step, the second endless belt 21 moves through the second circulation path along the second imaginary plane perpendicular to the moving surface 40a and parallel to the moving direction of the movement of the moving surface 40a. The second circulation path includes, on the upstream side, from the first reference segment 31x, in the conveyance direction of the continuous body 2, the second reference segment 21x in which the second endless belt 21 is adjacent to the imaginary line 2x of the continuous body 2 on the opposite side to the moving surface 40a when the first region 2a of the continuous body 2 is suction-held on the moving surface 40a. The second endless belt 21 moves, in the second reference segment 21x, in the same direction as the moving direction of the movement of the moving surface 40a at the same speed as the moving speed of the movement of the moving surface 40a.

(5) In the second guiding step, the second guide members 51a and 51b disposed along the second reference segment 21x come into contact with the adjacent portion of the second region 2b of the continuous body 2 adjacent to the suction-held portion, and move the adjacent portion of the second region 2b of the continuous body 2 toward the first region so that the angle between the first region 2a and the second region 2b of the continuous body 2 in the cross-section perpendicular to the imaginary line 2x of the continuous body 2 can be reduced toward the downstream side in the conveyance direction of the continuous body 2.

(6) In the opposing position shift detecting step, in a portion of the continuous body 2 having completed the first guiding step, the opposing position shift that is a shift in relative position between the sides of the side edges 2p and 2a and the side of the folding line (the side of the imaginary line 2x) of the continuous body 2 that should essentially oppose each other is detected.

(7) In the controlling step, if an opposing position shift beyond an acceptable level is detected in the opposing position shift detecting step, a first speed of the first endless belt 31 moving through the first reference segment 31x and a second speed of the second endless belt 21 moving through the second reference segment 21x are changed to be different from the moving speed of the movement of the moving surfaces 40a and 42a.

It is noted that the steps described in the above (6) and (7) may be omitted, or the steps described in the above (4) to (7) may be omitted.

In the above-described method, while the continuous body 2 is being conveyed with the first region 2a suction-held on the moving surfaces 40a and 42a in the conveying step, the angle between the first region 2a and the second region 2b is reduced in the first guiding step. Since the first endless belt 31 is adjacent to the imaginary line 2x of the continuous body 2 in the first reference segment 31x, the continuous body 2 can be folded along the imaginary line 2x of the continuous body 2. Since the first endless belt 31 moves through the first circulation path along the first imaginary plane including the moving surfaces 40a and 42a of the conveying part, the angle between the first region 2a and the second region 2b of the continuous body 2 can be made acute. Therefore, after completing the first folding reference step and the first guiding step, the second region 2b of the continuous body 2 can be easily folded over the first region 2a.

In the above-described method, even if the first endless belt 31 comes into contact with the continuous body 2 in the first reference segment 31x, the first endless belt 31 moves in the same direction at the same speed as the continuous body 2, and hence a force resistive to the conveyance of the continuous body 2 is not generated. A force resistive to the conveyance of the continuous body 2 can be a factor for disturbing the operation of folding the continuous body 2, but since such a force is not generated, the operation of folding the continuous body 2 can be easily stabilized.

When the method includes the steps described in the above (1) to (5), the segment in which the continuous body 2 is folded can be elongated, and thus the operation of folding the continuous body 2 can be more stabilized. Even if the second endless belt 21 comes into contact with the continuous body 2 in the second reference segment 21x, the second endless belt 21 moves in the same direction at the same speed as the continuous body 2, and hence a force resistive to the conveyance of the continuous body 2 is not generated. A force resistive to the conveyance of the continuous body 2 can be a factor for disturbing the operation of folding the continuous body 2, but since such a force is not generated, the operation of folding the continuous body 2 can be easily stabilized.

When the method includes the steps described in the above (1) to (7), in the occurrence of an opposing position shift that is a shift in relative position between the sides of the side edges 2p and 2q and the side of the folding line (the side of the imaginary line 2x) of the continuous body 2 that should essentially oppose each other in the portion of the continuous body 2 where the second region 2b is folded over the first region 2a, the opposing position shift can be eliminated.

CONCLUSION

As described so far, the folding device 10 can easily stabilize the operation of folding the continuous body 2.

It is noted that the present invention is not limited to the above-described embodiments, but can be practiced with various modifications.

For example, the present invention is applicable to a continuous body including no absorber disposed therein, or to a continuous body having no hole formed therein.

REFERENCE SIGNS LIST 2 continuous body
2a first region
2b second region
2x imaginary line
10 continuous body folding device
20 second folding reference part
21 second endless belt
21x second reference segment
30 first folding reference part
31 first endless belt
31x first folding reference part
40, 42 belt conveyor (conveying part)
40a, 42a moving surface
40m, 42m conveyance motor (conveying part)
41 conveying part
51a, 51b second guide member
51c to 51f first guide member
80 control unit
82 opposing position shift detection unit

The invention claimed is:

1. A continuous body folding device for folding a belt-shaped continuous body along a line of the continuous body that extends in a longitudinal direction of the continuous body so as to divide the continuous body into a first region and a second region, comprising:
a conveying part that has a moving surface suction-holding a portion of the first region of the continuous body so as to cause the moving surface to come into contact with a first main surface of the continuous body, the moving surface moving so as to convey the continuous body in the longitudinal direction thereof;
a first folding reference part that includes a first endless belt moving through a first circulation path, the first circulation path extending adjacent to the moving surface, the first circulation path including a first reference segment that extends in a direction parallel to a moving direction of the moving surface, from the first reference segment, the first endless belt coming into contact with a second main surface of the continuous body along the line of the continuous body, the first endless belt moving, in the first reference segment, in a direction identical to the moving direction of the moving surface at a speed identical to a moving speed of the movement of the moving surface;
a first guide member that is disposed along the first reference segment so as to, when viewed in a direction parallel to the moving direction of the moving surface, form an acute angle between the first guide member and the moving surface, the first guide member being disposed so as to cause the first reference segment to be disposed in the acute angle adjacent to an apex of the acute angle, the first guide member being disposed so as to come into contact with the first main surface of the second region of the continuous body, thereby the second region of the continuous body moving toward the suction-held portion of the first region of the continuous body while being conveyed;
a second folding reference part that includes a second endless belt moving through a second circulation path, the second circulation path being positioned before the first folding reference part with regards to the moving direction of the moving surface, the second circulation path extending along a plane that is parallel to the moving direction of the moving surface and is perpendicular to the moving surface, the second circulation path including a second reference segment, the second reference segment extending in the direction parallel to the moving direction of the moving surface, from the second reference segment the second endless belt coming into contact with the second main surface of the continuous body along the line of the continuous body, the second endless belt moving, in the second reference segment, in the direction identical to the moving direction of the moving surface at the speed identical to the moving speed of the movement of the moving surface; and
a second guide member that is disposed along the second reference segment so as to, when viewed in the direction parallel to the moving direction of the moving surface, form an obtuse angle between the second guide member and the moving surface, the second guide member being disposed so as to cause the second reference segment to be disposed in the obtuse angle adjacent to an apex of the obtuse angle, the second guide member being disposed so as to come into contact with the first main surface of the second region of the continuous body, thereby the second region of the continuous body moving toward the suction-held portion of the first region of the continuous body while being conveyed.

2. The continuous body folding device according to claim 1, further comprising:
an opposing position shift detection unit that detects, in a portion of the continuous body having passed through the first guide member, a shift in relative position between a side edge and the line of the continuous body; and
a control unit that changes the speed of the first endless belt and the speed of the second endless belt when the shift detected by the opposing position shift detection unit is beyond a predetermined level.

3. The continuous body folding device according to claim 1, wherein the first reference segment and the second reference segment are linearly disposed in the longitudinal direction of the continuous body,
the first endless belt of the first folding reference part and the second endless belt of the second folding reference part are formed separately from each other and extend perpendicular to each other, and
the first endless belt in the first reference segment folds the continuous body such that, when viewed in a direction perpendicular to the moving surface, the second region of the continuous body overlaps the first region of the continuous body, and the second endless belt in the second reference segment folds the continuous body such that, when viewed in the direction perpendicular to the moving surface, the second region of the continuous body is located outside the first region of the continuous body.

4. A continuous body folding method for folding a belt-shaped continuous body along a line of the continuous body that extends in a longitudinal direction of the continuous body so as to divide the continuous body into a first region and a second region, comprising:
a conveying step of suction-holding a portion of the first region of the continuous body on a moving surface so as to cause the moving surface to come into contact with a first main surface of the continuous body and convey the continuous body in the longitudinal direction thereof;
a first folding reference step of moving a first endless belt through a first circulation path that extends adjacent to the moving surface, the first circulation path including a first reference segment that extends in a direction parallel to a moving direction of the moving surface, from the first reference segment, the first endless belt coming into contact with a second main surface of the continuous body along the line of the continuous body, the first endless belt moving, in the first reference segment, in a direction identical to the moving direction of the moving surface at a speed identical to a moving speed of the moving surface;
a first guiding step of disposing a first guide member along the first reference segment so as to, when viewed in a direction parallel to the moving direction of the moving surface, form an acute angle between the first guide member and the moving surface, disposing the first guide member so as to cause the first reference segment to be disposed in the acute angle adjacent to an apex of the acute angle, and disposing the first guide member so as to come into contact with the first main surface of the second region of the continuous body, thereby the second region of the continuous body moving toward the suction-held portion of the first region of the continuous body while being conveyed;
a second folding reference step of moving a second endless belt through a second circulation path, the second circulation path being positioned before the first endless belt with regards to the moving direction of the moving surface, the second circulation path extending along a plane that is parallel to the moving direction of the moving surface and is perpendicular to the moving surface, the second circulation path including a second reference segment, the second reference segment extending in the direction parallel to the moving direction of the moving surface, form the second reference segment the second endless belt coming into contact with the second main surface of the continuous body along the line of the continuous body, the second endless belt moving, in the second reference segment, in the direction identical to the moving direction of the moving surface at the speed identical to the moving speed of the moving surface; and
a second guiding step of disposing a second guide member along the second reference segment so as to, when viewed in the direction parallel to the moving direction of the moving surface, form an obtuse angle between the second guide member and the moving surface, disposing the second guide member so as to cause the second reference segment to be disposed in the obtuse angle adjacent to an apex of the obtuse angle, and disposing the second guide member so as to come into contact with the first main surface of the second region of the continuous body, thereby the second region of the continuous body moving toward the suction-held portion of the first region of the continuous body while being conveyed.

5. The continuous body folding method according to claim 4, further comprising:
an opposing position shift detecting step of detecting, in a portion of the continuous body having completed the first guiding step, a shift in relative position between a side edge and the line of the continuous body; and
a controlling step of changing the speed of the first endless belt and the speed of the second endless belt when the shift detected in the opposing position shift detecting step is beyond a predetermined level.

6. The continuous body folding method according to claim 4, wherein in the second folding reference step, the second endless belt of the second folding reference part is moved separately from and extends perpendicular to the first endless belt of the first folding reference part such that the first reference segment and the second reference segment are linearly disposed in the longitudinal direction of the continuous body,
in the first guiding step, the first guide member is disposed such that, when viewed in a direction perpendicular to the moving surface, the second region of the continuous body overlaps the first region of the continuous body, and
in the second guiding step, the second guide member is disposed such that, when viewed in the direction perpendicular to the moving surface, the second region of the continuous body is located outside the first region of the continuous body.

* * * * *